United States Patent
Pruter

(10) Patent No.: US 7,087,024 B1
(45) Date of Patent: *Aug. 8, 2006

(54) METHOD AND APPARATUS FOR GUIDING NEEDLES

(76) Inventor: Rick L. Pruter, 21 Woodcrest La. NE., Iowa City, IA (US) 52240

( * ) Notice: Subject to any disclaimer, the term of this patent is extended or adjusted under 35 U.S.C. 154(b) by 0 days.

This patent is subject to a terminal disclaimer.

(21) Appl. No.: 10/250,149

(22) Filed: Jun. 6, 2003

Related U.S. Application Data

(63) Continuation of application No. 09/682,367, filed on Aug. 24, 2001, now Pat. No. 6,612,990, which is a continuation-in-part of application No. 09/526,048, filed on Mar. 15, 2000, now Pat. No. 6,296,614, which is a continuation-in-part of application No. 29/103,098, filed on Apr. 8, 1999, now Pat. No. Des. 424,693.

(51) Int. Cl.
*A61B 8/14* (2006.01)
(52) U.S. Cl. .................................. 600/461
(58) Field of Classification Search ........ 600/459–471, 600/407, 562; 604/118
See application file for complete search history.

(56) References Cited

U.S. PATENT DOCUMENTS

| | | | |
|---|---|---|---|
| 2,451,183 A | 10/1948 | Tantimonaco | |
| 2,536,963 A | 1/1951 | Stephens | |
| 3,017,887 A | 1/1962 | Heyer | |
| 3,538,915 A | 11/1970 | Frampton et al. | |
| 3,556,079 A | 1/1971 | Omizo | |
| 3,924,308 A * | 12/1975 | Duprez | 24/274 R |
| 4,029,084 A | 6/1977 | Soldner | |
| 4,058,114 A | 11/1977 | Soldner | |
| 4,108,165 A | 8/1978 | Kopp et al. | |
| 4,132,496 A | 1/1979 | Casto | |
| 4,249,539 A | 2/1981 | Vilkomerson et al. | |
| 4,289,139 A | 9/1981 | Enjoji et al. | |
| 4,332,248 A | 6/1982 | DeVitis | |
| 4,363,326 A | 12/1982 | Kopel | |
| 4,402,324 A | 9/1983 | Lindgren et al. | |
| 4,408,611 A | 10/1983 | Enjoji | |
| 4,414,908 A * | 11/1983 | Eguchi et al. | 112/169 |
| 4,469,106 A * | 9/1984 | Harui | 600/461 |
| 4,489,730 A | 12/1984 | Jingu | |
| 4,491,137 A | 1/1985 | Jingu | |
| 4,497,325 A | 2/1985 | Wedel | |
| 4,504,269 A | 3/1985 | Durand | |
| 4,542,747 A | 9/1985 | Zurinski et al. | |
| 4,635,644 A | 1/1987 | Yagata | |
| 4,773,288 A * | 9/1988 | Jang et al. | 81/409.5 |
| 4,781,067 A | 11/1988 | Cichanski | |
| 4,898,178 A | 2/1990 | Wedel | |
| 4,899,756 A * | 2/1990 | Sonek | 600/461 |
| 4,970,907 A | 11/1990 | Flynn | |

(Continued)

OTHER PUBLICATIONS

Affidavit of Applicant Admitted Prior Art, Toshiba Product Description UAGV021A.

*Primary Examiner*—Francis J. Jaworski
(74) *Attorney, Agent, or Firm*—Simmons Perrine Albright & Ellwood PLC

(57) ABSTRACT

An apparatus and method for guiding a needle in conjunction with a biopsy using a medical imaging device, where an open-ended needle guide with an adjustable slidable multi-gauge needle stop is used to guide a needle during insertion and during a tilting of the needle with respect to the medical imaging device.

9 Claims, 2 Drawing Sheets

U.S. PATENT DOCUMENTS

| | | |
|---|---|---|
| 5,052,396 A | 10/1991 | Wedel et al. |
| 5,076,279 A * | 12/1991 | Arenson et al. ............ 600/461 |
| 5,088,500 A | 2/1992 | Wedel et al. |
| 5,161,764 A | 11/1992 | Roney |
| 5,235,987 A | 8/1993 | Wolfe |
| 5,300,082 A * | 4/1994 | Sharpe et al. ............... 606/147 |
| 5,343,865 A | 9/1994 | Gardineer et al. |
| D362,064 S | 9/1995 | Smick |
| 5,623,931 A | 4/1997 | Wung et al. |
| D383,968 S | 9/1997 | Bidwell et al. |
| 5,758,650 A | 6/1998 | Miller et al. |
| 5,871,448 A | 2/1999 | Ellard |
| 5,910,113 A | 6/1999 | Pruter |
| 5,924,992 A * | 7/1999 | Park et al. ................... 600/461 |
| 5,941,889 A | 8/1999 | Cermak |
| D424,693 S | 5/2000 | Pruter |
| 6,095,981 A * | 8/2000 | McGahan ................... 600/461 |
| 6,139,544 A | 10/2000 | Mikus et al. |
| 6,203,499 B1 | 3/2001 | Imling et al. |
| 6,238,336 B1 * | 5/2001 | Ouchi ........................ 600/160 |
| 6,296,614 B1 | 10/2001 | Pruter |
| 6,311,084 B1 | 10/2001 | Cormack et al. |
| 6,379,307 B1 | 4/2002 | Filly et al. |
| 6,475,152 B1 * | 11/2002 | Kelly et al. .................. 600/461 |
| 6,612,990 B1 * | 9/2003 | Pruter ........................ 600/461 |

* cited by examiner

METHOD AND APPARATUS FOR GUIDING NEEDLES

CROSS REFERENCE TO RELATED APPLICATIONS

The present application is a continuation of application Ser. No. 09/682,367 entitled "Method and apparatus for guiding needles", filed by the same inventor on Aug. 24, 2001, and now U.S. Pat. No. 6,612,990, and which application itself was a continuation-in-part application of an application entitled "Needle guide for attachment to ultrasound transducer probe" by the same inventor, the application having Ser. No. 09/526,048 which was filed on Mar. 15, 2000, and issued as U.S. Pat. No. 6,296,614 on Oct. 2, 2001, which itself was a continuation-in-part of application 29/103,098, also entitled "Needle guide for attachment to ultrasound transducer probe" filed on Apr. 8, 1999, which issued as U.S. Pat. No. Des. 424,693 on May 9, 2000. The above-referenced application, Patent and U.S. Design Patent are incorporated herein in their entirety by these references.

BACKGROUND OF INVENTION

In recent years, handheld medical imaging transceivers, such as ultrasound and gamma ray transceivers, have been used extensively for various medical imaging situations. In certain procedures, such as biopsies, it may be desired to tilt a needle with respect to a needle guide or vice versa.

In the past, the physician or medical professional may be required to detach a biopsy needle from a needle guide prior to changing the angle of the needle with respect to the needle guide and transceiver. Other prior art needle guides have included a pair of spaced-apart fixed parallel plates. The medical professional could place the needle between the parallel plates, and it would be free in a plane parallel with the plates, but restricted from large movements outside that plane.

Other prior art needle guides have been used which include a resilient tube coupled to a transducer where the tube has a longitudinal slit through which the needle can be pulled when relative tilting is required.

While these needle guides have been used extensively in the past, they do have some drawbacks. First of all, any model of fixed parallel plate needle guide is limited in the size of needle that can be guided therein. If the needle is too big, it will not fit between the fixed parallel plates. If the plates are too far apart, there is less support being provided in the desired direction. Also, these parallel plate needle guides only provide support in one direction. They provide no support or resistance from motion within the plane of the parallel gap between the fixed plates. This increases the attention required by the medical professional.

Secondly, the resilient slit tube type of needle guide does provide some resistance to motion in the desired plane of motion, but it is limited to only the first portion of that movement or motion. Once the needle is tilted out of the tube, there is no support or resistance to motion in any direction. Additionally, these types of needle guides will work only with specific gauges of needles. They will not work well when a narrow gauge needle is used in a needle guide primarily designed for a larger needle. The narrower needle may fall through the slit. Conversely, a larger needle may not fit in the tube, or it may be difficult to pull through the slit. Consequently, numerous sized slit tube needle guides would be needed to fulfill the needs of a medical professional who uses needles of varying sizes. Additionally, these slit tube type of needle guides may be viewed as unstable in the direction of relative motion. For example, the force required to be applied to the needle to move the needle in the tilted direction decreases as the amount of tilting occurs. To assure that excess tilting does not occur, the medical professional needs to give more attention to the force being applied when the required force decreases with angular displacement.

Consequently, there exists a need for improved methods and apparatus for guiding needles in an efficient manner.

SUMMARY OF INVENTION

It is an object of the present invention to provide an apparatus and method for guiding a tiltable needle in an efficient manner.

It is a feature of the present invention to utilize a multi-gauge adjustable needle guide.

It is another feature of the present invention to include a slidable needle stop.

It is another feature of the present invention to include a slide-ably adjustable needle guide stop with a bias force for closing the needle guide.

It is another feature of the present invention to include needle stops having contours for engaging needles.

It is an advantage of the present invention to achieve improved efficiency in guiding needles.

The present invention is an apparatus and method for guiding needles designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of tilting has been greatly reduced.

Accordingly, the present invention is an apparatus and method including a slidable needle stop in a multi-gauge adjustable needle guide.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
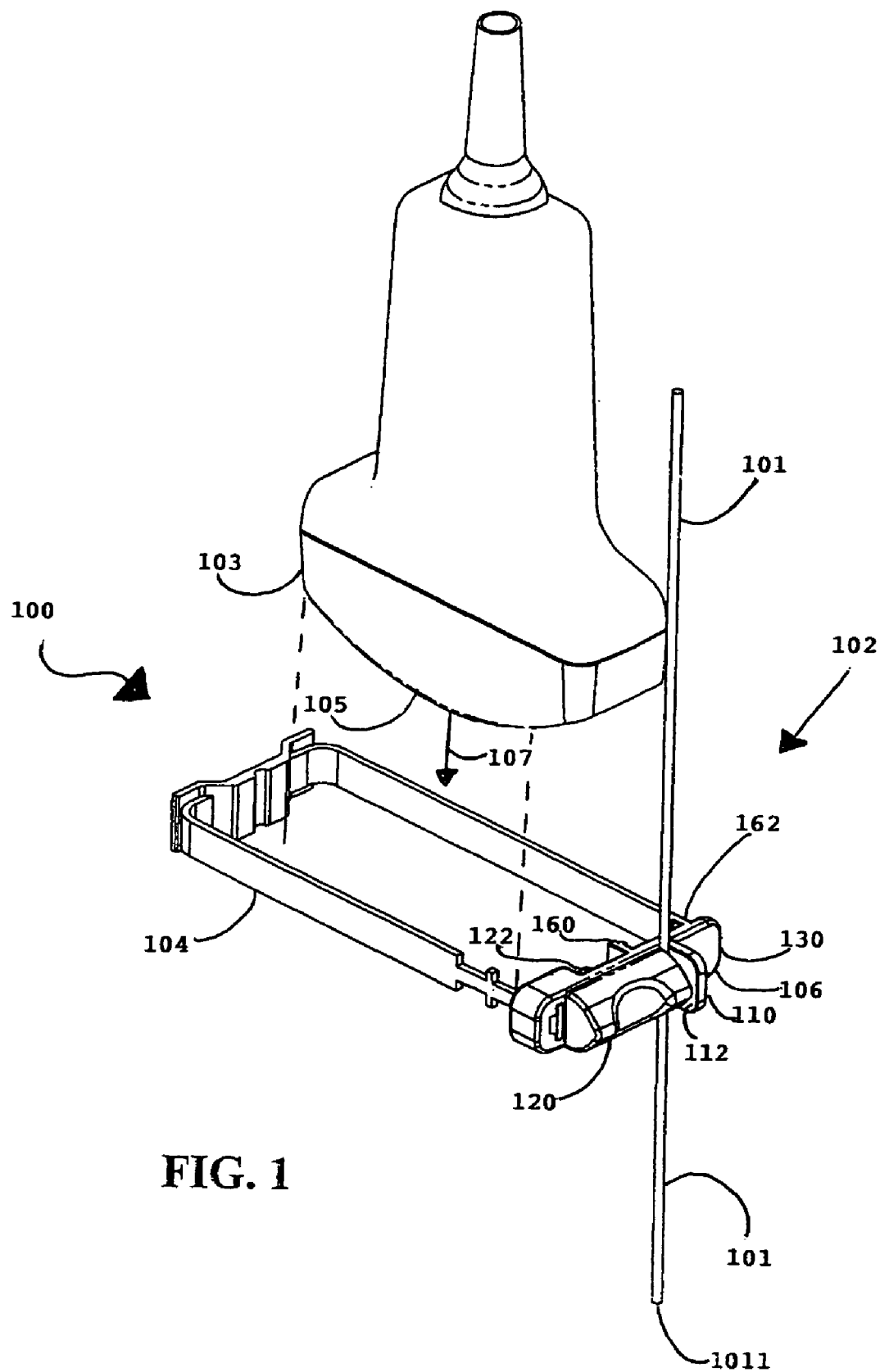
FIG. 1 is a partially exploded perspective view of the apparatus of the present invention.

Now referring to the drawings wherein like numerals refer to like matter throughout, and more specifically referring to FIG. 1, there is shown a needle guide assembly 100, of the present invention which includes a needle guide 102 with a needle 101 disposed therein. Needle guide 102 is coupled to medical imaging device 103, which could be an ultrasound transducer, gamma ray transceiver or other imaging device, via a medical imaging device retaining strap 104, which could be an elastic strap, such as rubber or a less elastic strap, such as fabric or leather. Cables, wires, rope, brackets, clamps or any other suitable substitute could be used for a medical imaging device retaining strap 104. Needle guide 102 is preferably a plastic material, such as ABS or equivalent; however, other materials, such as aluminum, surgical steel, and any other suitable material could be substituted.

The medical imaging device 103 has a transmitting end 105, which may be a planar face with a vertical axis 107 extending orthogonally therefrom.

The term "vertical axis 107" is used herein to convey that the axis is orthogonal to the transmitting surface end 105. Depending on the orientation of the medical imaging device 103, the vertical axis 107 may be pointed in any direction with respect to the patient or an earth reference. In normal operation, the medical imaging device 103 is often held, at least at first, with the transmitting end 105 in a substantially horizontal (earth reference) arrangement. This arrangement results in the vertical axis 107 being orientated in a vertical (earth reference) direction.

Needle guide 102 has a slidable needle stop 120 which may be contoured on its top side to facilitate engagement with a human finger or thumb. Slidable needle stop 120 is preferably slidable along needle guide main body 106 which contains a first needle stop 110. However, other arrangements between the slidable needle stop 120 and first needle stop 110 could be substituted. First needle stop 110 may be vertical and have a planar needle engagement surface 112 as shown, but other arrangements could be employed as well.

Also shown in FIG. 1 are members 160 and 162, which can form a pliable clip for attaching needle guide 102 to a bracket (not shown) coupled to a medical imaging transceiver when strap 104 is not used.

Figure 2:
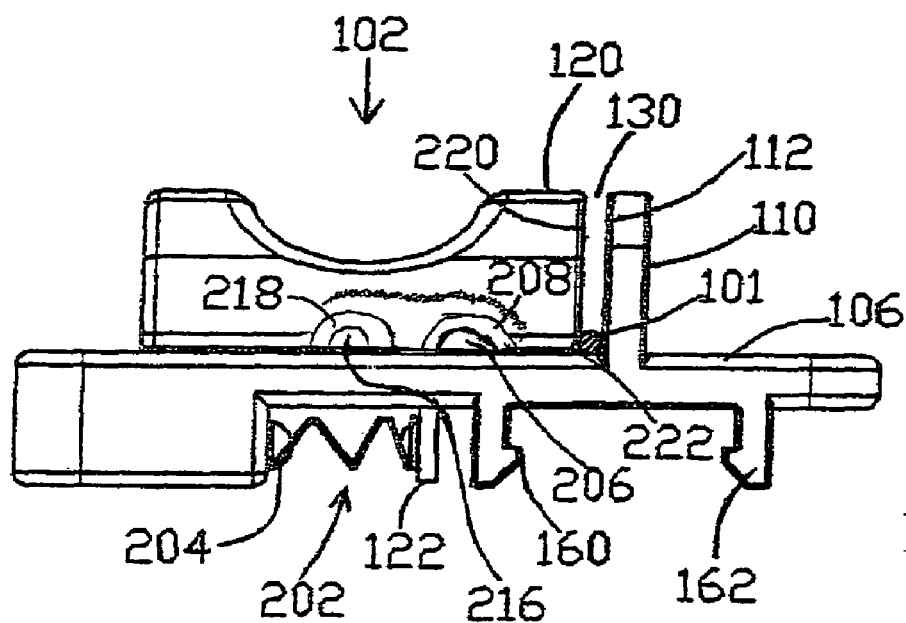
FIG. 2 is an enlarged partially cut-away side view of the needle guide of FIG. 1, where the cut-away portion exposes a plurality of detent mechanisms.

Now referring to FIG. 2, there is shown a partially cut-away side view of the needle guide 102 of FIG. 1. Needle guide 102 is shown having a spring 202, which could be a simple metal or plastic spring, or it could be any resilient member or other apparatus capable of biasing sliding spring stop 122 so as to tend to minimize the width of needle gap 130. Spring 202 is shown disposed between fixed spring stop 204 and sliding spring stop 122. Needle guide 102 is also shown in the cut-away portion as having a needle guide main body 106, first detent protrusion 206 and second detent protrusion 216 which are received by first detent protrusion receiving void 208 and second detent protrusion receiving void 218 both found in slidable needle stop 120. Slidable needle stop 120 is shown having a top leading edge 220 and a bottom angled leading edge 222. Preferably, the pressure exerted by spring 202 is sufficient to hold needle 101 stationary unless a force other than gravity acts upon it.

Figure 3:
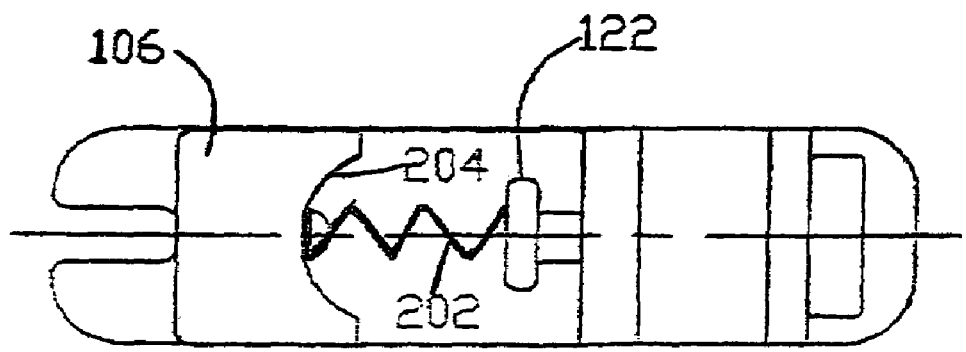
FIG. 3 is a bottom view of the needle guide of FIGS. 1 and 2.

Now referring to FIG. 3, there is shown a bottom view of the needle guide 102 of FIGS. 1 and 2.

In operation, the apparatus and method of the present invention as described and shown in FIGS. 1–3, could function as follows:

Needle guide 102 is attached to medical imaging device 103 via medical imaging device retaining strap 104. The needle guide 102 is readied for receipt of the needle 101 by sliding slidable needle stop 120 to create a gap sufficiently large to accommodate the particular biopsy needle used. The biopsy needle, such as needle 101, is inserted into needle gap 130 and slidable needle stop 120 is released, thereby holding needle 101. The needle 101 is then inserted into the patient. Medical imaging device 103 is used to create a first image of a portion of a human body. The medical imaging device 103 and needle guide 102 are then tilted with respect to the needle 101. This provides a different angle of view of the end 1011 of the needle 101. A second image is then created by the medical imaging device 103. The needle may be held stationary and the medical imaging device 103 and needle guide 102 tilted, or vice versa.

The tilting of the needle 101 or needle guide 102 is done by applying a force between the two. As the angle of separation between the vertical axis 107 and the longitudinal axis of the needle 101 increases, the amount of contact between the needle 101 and planar needle engagement surface 112 and top leading edge 220 increases. This increases the friction on the needle 101, thereby increasing the force needed to move the needle 101 to larger angular separations with respect to the needle guide 102.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

Throughout this document, references are made to "vertical" and "horizontal". These terms are intended to mean "substantially vertical" and "substantially horizontal". Minor deviations from vertical and minor deviations from horizontal are intended to be included therein. Also see the above definition on vertical axis 107.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

The invention claimed is:

1. A system for guiding a needle comprising:
   a medical imaging transceiver, configured to generate signals representative of an internal portion of a human body;
   a first needle stop having a first needle engagement surface;
   a slidable needle stop having a leading edge opposing said needle engagement surface so as to form a needle gap therebetween;
   said slidable needle stop being slidable so as to provide said needle gap with a variable gap width;
   said first needle stop and said slidable needle stop being configured to form an open ended slot which permits a needle disposed in said needle gap to be removed from said needle gap when said needle is pivoted; and
   an elongated flexible strap being elastic along a longitudinal axis, further being conformable so as to wrap around at least a portion of the medical imaging transceivers, where a shape characteristic of the medical imaging transceiver is one of a variety of shapes;
   WHEREBY said first needle stop and said slidable needle stop are configured to cooperate to provide needle engaging forces upon a needle when said needle is disposed in said needle gap and simultaneously configured to permit removal of said needle from said needle gap by pivoting said needle in a direction orthogonal to a needle axis, and the first needle stop and the slidable needle stop are held in place adjacent to the medical imaging transceiver by at least the elongated flexible strap.

2. A system of claim 1 wherein said slidable needle stop is biased so as to minimize said needle gap.

3. A system of claim 1 wherein said slidable needle stop is spring biased.

4. A system of claim 1 wherein said slidable needle stop is spring biased so as to minimize said variable gap width.

5. A system of claim 1 wherein said slidable needle stop is configured to slide to a plurality of predetermined positions such that said variable gap width is different for each of said plurality of predetermined positions.

6. A system of claim 5 further comprising a plurality of detents on an interface between said slidable needle stop and a body.

7. A needle guide comprising:
a medical imaging transceiver;
a first needle stop, having a first needle engagement surface;
a second needle stop having a second needle engagement surface;
a needle receiving gap formed by said first needle receiving surface and said second needle receiving surface;
said needle receiving gap having an open end, such that a needle, having a longitudinal axis, disposed therein can be tilted in tilt direction orthogonal to the longitudinal axis and can be tilted beyond a limit of one of said first needle stop and said second needle stop; so that the needle can be displaced from said needle receiving gap;
said first needle stop and said second needle stop being configured to permit relative movement therebetween, so as to provide adjustment of forces being applied to said needle; and
an elastic belt configured to wrap around a portion of the medical imaging transceiver and to hold the first needle stop at a fixed location with respect to the medical imaging transceiver.

8. A needle guide of claim 7 wherein a biasing force is applied to one of said first needle stop and said second needle stop so that said needle tends to remain stationary unless acted upon by a force other than gravity.

9. A method of imaging comprising the steps of:
providing a medical imaging transceiver;
disposing a needle, having a longitudinal axis, in a needle guide which has an adjustable needle gap width;
the needle guide being coupled to the medical imaging transceiver having a vertical axis, via an elongated elastic belt which wraps around and conforms to an exterior surface of the medical imaging transceiver;
causing said needle to enter a human body at a first angle with respect to said vertical axis;
applying a tilting force between said needle and said needle guide to overcome a frictional force; and,
said tilting force causing a relative tilting of said needle with respect to said first angle.

* * * * *